United States Patent [19]

Misra et al.

[11] Patent Number: 4,965,279

[45] Date of Patent: Oct. 23, 1990

[54] CYCLOPROPYL AZA PROSTAGLANDIN ANALOGS

[75] Inventors: Raj N. Misra, Hopewell; David M. Floyd, Pennington; Steven E. Hall, Ewing Township, Mercer County, all of N.J.

[73] Assignee: E. R. Squibb & Sons, Inc., Princeton, N.J.

[21] Appl. No.: 272,953

[22] Filed: Nov. 18, 1988

[51] Int. Cl.$^5$ .................... A61K 31/41; C07C 69/74
[52] U.S. Cl. ..................... 514/381; 260/401; 260/402.5; 260/404; 514/531; 514/560; 514/562; 514/563; 514/564; 514/567; 514/601; 514/602; 514/604; 514/605; 548/253; 548/254; 560/9; 560/12; 560/13; 560/37; 560/42; 560/118; 560/124; 562/426; 562/427; 562/430; 562/442; 562/451; 562/500; 562/506; 564/80; 564/83; 564/84; 564/89; 564/91; 564/98; 564/99
[58] Field of Search ............. 560/12, 13, 9, 42, 37, 560/118, 124; 562/426, 427, 430, 451, 442, 500, 506; 564/80, 89, 91, 84, 98, 99; 514/381, 531, 562, 563, 564, 567, 602, 604, 600, 605, 560; 548/253, 254; 260/401, 402.5, 404

[56] References Cited

U.S. PATENT DOCUMENTS 4,663,336  5/1987  Nakane et al. ................. 514/381

FOREIGN PATENT DOCUMENTS 3518721  11/1986  Fed. Rep. of Germany .

*Primary Examiner*—Michael L. Shippen
*Attorney, Agent, or Firm*—Theodore R. Furman, Jr.

[57] ABSTRACT

Novel cyclopropyl aza prostaglandin analogs are disclosed having the formula

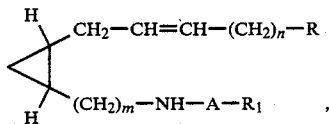

wherein A can be carbonyl, sulfonyl or a single bond.

These compounds are useful, for example, as thromboxane antagonists.

13 Claims, No Drawings

CYCLOPROPYL AZA PROSTAGLANDIN ANALOGS

FIELD OF THE INVENTION

The present invention relates to cyclopropyl aza prostaglandin analogs and more particularly concerns such compounds which are useful, for example, in the treatment of thrombotic and/or vasospastic disease.

BACKGROUND OF THE INVENTION

German Patent Application 3518-271-A discloses hydroxy alkenyl cyclopropane derivatives of the formula

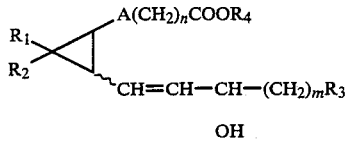

wherein A can be —CH=CH— or

$R_1$, $R_2$ and $R_4$ can be hydrogen or alkyl of 1 to 6 carbons;

$R_3$ can be 1) alkyl or alkenyl of 1 to 8 carbons, optionally substituted by halogen or alkyl of 1 to 2 carbons;

2) cycloalkyl or cycloalkenyl of 3 to 7 carbons;

3) aryl or aryloxy of 6 to 10 carbons, optionally substituted with halogen or alkyl or haloalkyl, each of 1 to 2 carbons; or 4) 5- or 6-membered heteroaryl or heteroaryloxy;

n is an integer from 1 to 6; and, m is zero or an integer from 1 to 4.

These compounds are described as having thromboxane antagonist and lipoxygenase inhibition activity.

SUMMARY OF THE INVENTION

In accordance with the present invention novel compounds useful, for example, as thromboxane antagonists, are disclosed. The cyclopropyl aza prostaglandin analogs of the present invention have the general formula

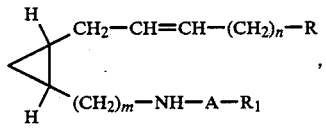

including pharmaceutically acceptable salts thereof, and all stereoisomers thereof, wherein

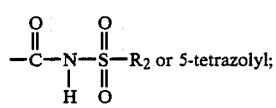

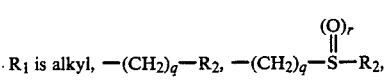

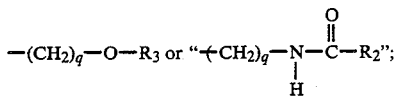

$R_2$ is aryl, alkyl or cycloalkyl;

$R_3$ is aryl, alkyl, cycloalkyl or acyl;

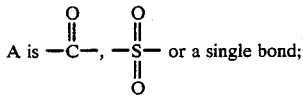

m is an integer from 1 to 2;

n is an integer from 2 to 4;

q is an integer from 1 to 4, except when A=single bond then q is an integer from 2–4; and r is zero or an integer from 1 to 2.

DETAILED DESCRIPTION OF THE INVENTION

The term "alkyl" as employed herein by itself or as part of another group refers to straight or branched chain hydrocarbon radicals of up to 12 carbon atoms, preferably 1 to 8 carbon atoms.

The $(CH_2)_m$ and $(CH_2)_n$ groups may be optionally substituted with one or two alkyl and/or one or two alkoxy substituents.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 haolgens, 1 or 2 lower alkyl groups and/or 1 or 2 lower alkoxy groups.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, 1 or 2 halogens (Cl, Br or F), and/or 1 or 2 lower alkoxy groups.

The term "acyl" as used herein by itself or as part of another group refers to groups including a

moiety.

The term "alkali metal" refers to metals such as sodium, potassium and lithium.

The term "halogen" or "halo" as used herein by itself or as part of another group refers to chlorine, bromine, fluorine or iodine with chlorine being preferred.

To prepare the compounds of formula I wherein A is

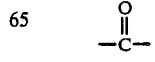

and R is

a starting material of the formula

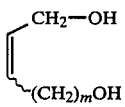                              II is treated with a base, such as sodium hydride, in the presence of a solvent, such as tetrahydrofuran, and thereafter reacted with a silyl-containing oxygen protecting group Prot, such as t-butyldimethylchlorosilane, t-butyldiphenylchlorosilane, dimethyl-thexylchlorosilane and the like, to provide a compound of the formula

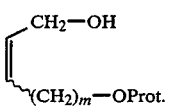                              III

Compound III can thereafter be treated with a cyclopropanation agent, such as methylene iodide, in the presence of iodine, Zn(Cu) and a solvent, such as dry ether, to provide a compound of the formula

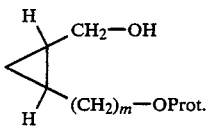                              IV

Compound IV can then be subjected to an oxidizing agent, e.g. Dess-Martin periodinane or pyridinium chlorochromate, in the presence of a solvent, such as methylene chloride, to provide the aldehyde

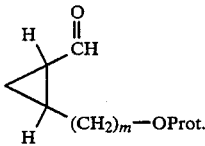                              V

Compound V is next subjected to a Wittig reaction via treatment with an alkoxymethyltriphenylphosphonium halide, such as (methoxymethyl)triphenylphosphonium chloride, in the presence of a base, e.g. potassium t-amylate, and in a solvent, such as tetrahydrofuran, to provide the enol ether of the formula

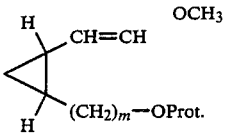                              VI

Treatment of a compound of formula VI in a solvent, such as tetrahydrofuran, with aqueous acid solution, such as hydrochloric acid, provides a compound having the formula

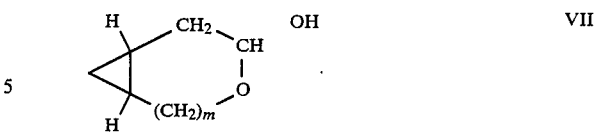                              VII

Treatment of compounds of formula VII with a carboxyalkyltriphenylphosphonium halide of the formula

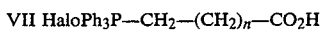

VII  HaloPh$_3$P—CH$_2$—(CH$_2$)$_n$—CO$_2$H    VII in solvents, such as tetrahydrofuran and toluene, and in the presence of a base, e.g., potassium t-amylate, followed by treatment with a diazoalkylene provides compounds of the formula

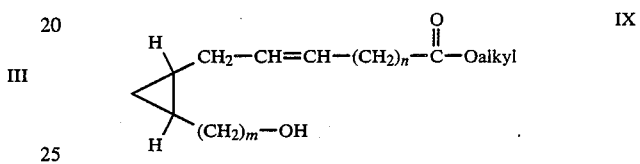                              IX

Reaction of compound IX in methylene chloride, with phthalimide, X,

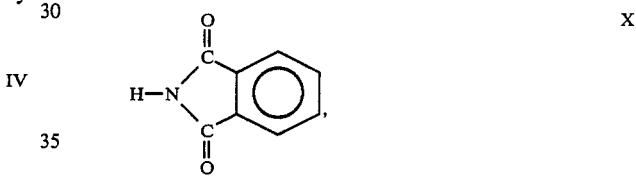                              X in the presence of activating agents, such as diisopropylazodicarboxylate and triphenylphosphine, provides

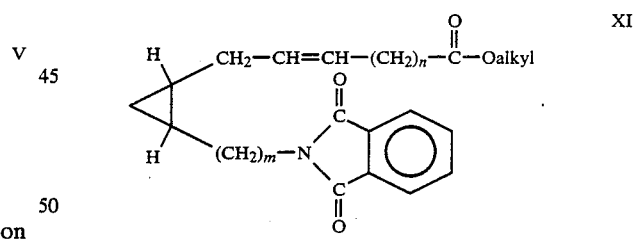                              XI

Selective hydrolysis of compound XI in a solvent mixture, e.g., methanol/methylene chloride, with anhydrous hydrazine followed by acidification with hydrochloric acid provides a compound of the formula

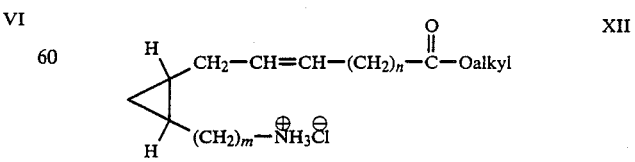                              XII

Compound XII, in a solvent such as methylene chloride, can thereafter be coupled to a compound of the formula

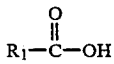

in the presence of an organic base, e.g., triethylamine, and a coupling agent, e.g. carbonyl diimidazole or dicyclohexylcarbodiimide, to provide compounds of the formula

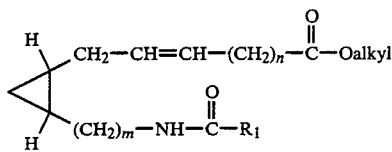

that is, compounds of formula I wherein A is

and R is

A compound of formula XIV, in a solvent mixture such as tetrahydrofuran and water, can be treated with an hydroxide base, e.g., lithium hydroxide monohydrate, then acidified with aqueous hydrochloric acid to provide

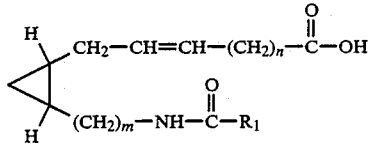

that is, compounds of formula I wherein A is

and R is

Treatment of a compound of formula XV with an alkali metal hydroxide, such as lithium hydroxide or sodium hydroxide, in the presence of aqueous tetrahydrofuran, provides compounds

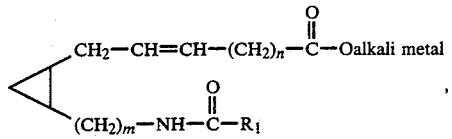

that is, compounds of formula I wherein A is

and R is

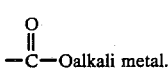

To prepare the compounds of formula I wherein A is

an intermediate of formula XII is reacted with a sulfonyl chloride of the formula

in the presence of a tertiary amine base, such as triethylamine or diisopropylethylamine, to provide a compound of the formula

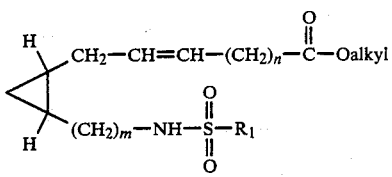

that is, compounds of formula I wherein A is

and R is

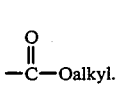

Compounds of formula I wherein A is

and R is

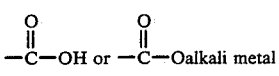

can be prepared from compound XVIII utilizing the methodology described above for compounds XV and XVI, respectively.

To prepare the compounds of formula I wherein A is a single bond, an intermediate of formula IX can be treated with an oxidizing agent, such as Dess-Martin periodinane or pyridinium chlorochromate in methylene chloride, to give the aldehyde of the formula

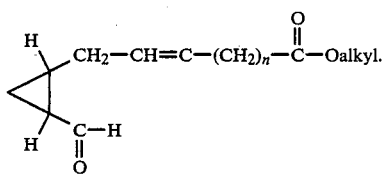   XIX

Reductive amination of AIX in methanol with an amine, $R_1NH_2$, in the presence of a reducing agent, such as sodium cyanoborohydrate at a pH of 3-5 adjusted with glacial acetic acid yields

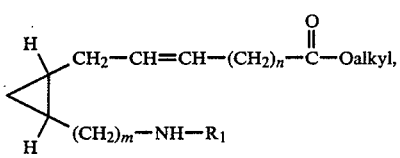   XX that is, compounds of formula I wherein A is a single bond and R is

Compounds of formula I wherein A is a single bond and R is either

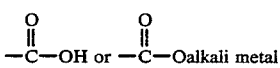

can be prepared from compound XX using the methodology described above for compounds XV and XVI, respectively.

To prepare the compounds of formula I wherein R is 5-tetrazolyl, compound IX is protected by treatment with a silyl-containing oxygen-protecting group Prot, such as t-butyldimethyl chlorosilane or t-butyldiphenyl chlorosilane to provide a compound of the formula

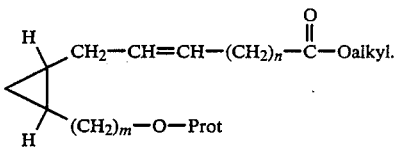   XXI

Compound XXI is subjected to an ammonolysis reaction by treatment with methanolic ammonia followed by a dehydration using, for example, p-toluenesulfonyl chloride and pyridine at 80°-100° C. to provide a compound of the formula

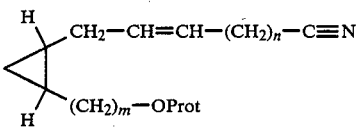   XXII which is deprotected by treatment with catalytic strong acid, such as concentrated HCl, in methanol, or aqueous hydrofluoric acid in acetonitrile, to provide the alcohol

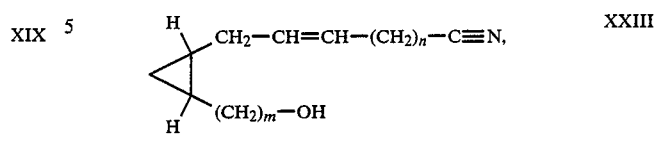   XXIII

Compound XXIII is then converted using the methodology described above for compounds XIV, XVIII and XX to yield

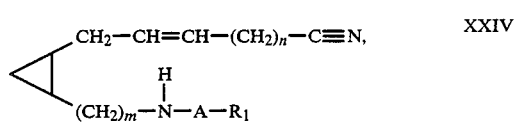   XXIV which is subjected to a cycloaddition reaction with sodium azide, in the presence of ammonium chloride in a polar solvent such as dimethylformamide at temperatures from 100°-130° C. to yield

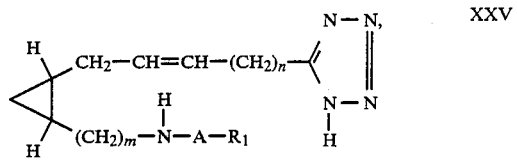   XXV that is, the compounds of formula I wherein R is 5-tetrazolyl.

To prepare the compounds of formula I wherein R is

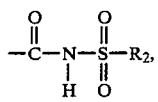

and A is

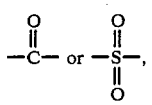

compounds of formula I where $R=CO_2H$ and

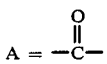

or $A=SO_2$, are treated with a sulfonamide of formula

   XXVI in the presence of a coupling agent, such as dicyclohexylcarbodiimide or carbonyldiimidazole in the presence of an amine, such as 4-dimethylaminopyridine to yield

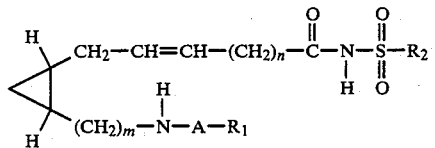 XXVII

To prepare the compounds of formula I wherein R is

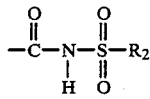

and A is a single bond, compound XX is protected, for example as the t-butylcarbamate, and is then subjected to the coupling reaction described above for compound XV, and deprotected, for example, with trifluoroacetic acid, to yield

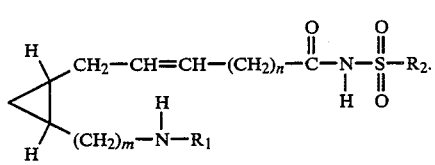 XXVIII

Preferred compounds of the present invention are those wherein

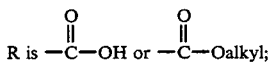

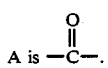

Most preferred compounds of the present invention are those wherein

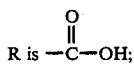

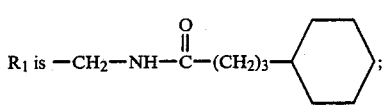

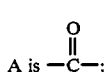

m=1; and,
n=2 or 3.

The present invention is meant to encompass the various stereoisomers of formula I which can be illustrated as follows.

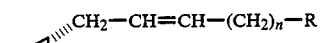 Ia

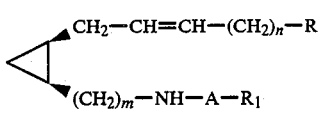 Ib

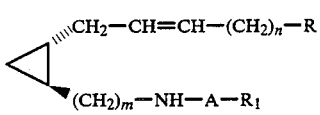 Ic

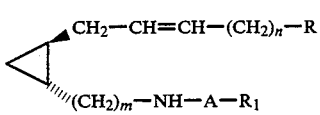 Id

The compounds of this invention are cardiovascular agents useful as platelet aggregation inhibitors, such as in inhibiting arachidonic acid-induced platelet aggregation e.g., for treatment of thrombotic disease such as coronary or cerebral thromboses, and in inhibiting bronchoconstriction. They are also thromboxane $A_2$ receptor antagonists, e.g., having a vasodilatory effect for treatment of myocardial ischemic disease, such as angina pectoris.

The compounds of this invention may also be used in combination with a cyclic AMP phosphodiesterase (PDE) inhibitor such as theophylline or papaverine in the preparation and storage of platelet concentrates.

In addition, the compounds of the invention may be useful in improving post-ischemic myocardial dysfunction, for example, decreased contractile dysfunction and decrease in tissue necrosis, preventing or treating toxemia in pregnancy, preventing or reducing platelet loss during extracorporeal circulation, preventing or reducing adverse reactions to protamine, preventing or reducing venous thrombosis (in conjunction with heparin), treating burn injury and in promoting wound healing, treating migrane headaches, treating ischemia (in combination with a calcium channel blocker), preserving vascular potency and circulation during vascular microsurgery, preventing reperfusion injury after CNS ischemic states like stroke or vascular surgery, treating tardive dyskinesia) treating hypertension, treating or preventing atherosclerosis, treating Raynard's Disease, treating unstable angina, treating purpura fulminarus, and treating thrombotic thrombocytopenia purpura. In addition, the compounds of the invention may be useful in the treatment of pulmonary embolism, diabetic retinopathy, ulcers, inflammation, arthritis, nephritis and in coronary artery bypass, angioplasty, renal dialysis, thrombolysis, endarterectomy and in treating or preventing complications following organ transplant (particularly cardiac or renal).

The compounds of the present invention may also be used in combination with a thrombolytic agent, such as t-PA, streptokinase, urokinase and the like, in the treatment of the above diseases, conditions or procedures.

The compounds of the invention can be administered orally or parenterally to various mammalian species known to be subject to such maladies, e.g., humans, cats, dogs and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. Alternatively, the compounds of the invention can be administered in a topical form (about 0.01 to about 5 percent by weight of compounds of formula I, 1 to 5 treatments daily) for wound healing. They may be compounded in conventional matter with a physiologically acceptable vehicle or carrier, excipient, binder, preservative, stabilizer, flavor, etc., as well as with a topical carrier such as Plastibase (mineral oil gelled with polyethylene), as called for by accepted pharmaceutical practice. Also as indicated in the discussion above, certain members additionally serve as intermediates for other members of the group.

The compounds of the invention may also be administered topically to treat peripheral vascular diseases and as such may be formulated as a cream or ointment.

The following Examples represent preferred embodiments of the present invention, however, the invention is not meant to be limited by the details described therein.

EXAMPLE 1

[1α(Z),2α]-7-[2-[[[[(4-Cyclohexyl-1-oxo-butyl)amino]acetyl]amino]methyl]cyclopropyl]-5-heptenoic acid, methyl ester

A.

(Z)-4-[(1,1-Dimethylethyl)dimethylsilyl]oxy]-2-buten-1-ol

To a mixture of 2.0 g of sodium hydride in 60 mL of dry tetrahydrofuran was added dropwise a solution of 4.1 mL (50 mMol), of 2-butene-1,4-diol in 30 mL of tetrahydrofuran over 15 minutes. The reaction was stirred for 30 minutes then heated with a warm water bath for 30 minutes. To the resulting mixture at room temperature was added 7.5 g (50 mMol) of t-butyldimethylchlorosilane over ~1 minute. The resulting mixture was stirred for 45 minutes then partitioned between 200 mL of ether and 100 mL of saturated aqueous sodium bicarbonate solution. The organic layer was separated, dried over anhydrous magnesium sulfate and concentrated in vacuo to give an oil. The crude material was purified by bulb-to-bulb distillation (140° /7mm) to afford 9.5 g (47 mMol) of the title A compound as a colorless liquid.

B.

(cis)-2-[[[(1,1-Dimethylethyl)dimethylsilyl]oxy]methyl]cyclopropanemethanol

To a mixture of 8.36 g of zinc-copper (128 mMol, Org. Synthesis, 41, 72 (1961)) in 75 mL of dry ether was added -150 mg of iodine. The reaction was stirred for 10 minutes then 9.6 mL (119 mMol) of methylene iodide was added and refluxed for 1 hour. To the resulting slurry 8.55 g (42.3 mMol) of the title A compound was added. Several milliliters of wet ether was introduced and after several minutes an exothermic reaction initiated which was controlled with external cooling. The reaction was then heated to reflux for an additional 1.5 hours followed by cooling in an ice-bath and dropwise addition of 11 mL (136 mMol) of pyridine. The resulting slurry was stirred for 15 minutes then filtered through Celite. The filtrate was washed rapidly with 100 mL 1M aqueous hydrochloric acid, then 100 mL aqueous sodium hydroxide, dried over anhydrous magnesium sulfate and concentrated in vacuo to give an oil. The crude material was purified by flash chromatography to afford 5.65 g (26.2 mMol) of the title B compound as a colorless oil.

C.

(cis)-2-[[[(1,1-Dimethylethyl)dimethylsilyl]oxy]methyl]cyclopropanecarboxaldehyde To a slurry of 9.41 g (22.2 mMol) of Dess-Martin periodinane in 60 mL of dry methylene chloride was added over 15 minutes a solution of 4.00 g (18.5 mMol) of the title B compound in 5 mL of methylene chloride. The reaction was stirred for 30 minutes then 200 mL of hexane was added and the mixture cooled in an ice-bath for 10 minutes. The resulting slurry was filtered and the filtrate concentrated in vacuo. The residue was slurried with 60 mL of hexane, cooled in an ice-bath for 30 minutes and then filtered. The filtrate was concentrated in vacuo to afford 3.98 g (18.5 mMol) of the title C compound as a colorless liquid.

D.

(cis)-2-[[[(1,1-Dimethylethyl)dimethylsilyl]oxymethyl]-1-(2-methoxyethenyl)cyclopropane To a slurry of 10.0 g (26.2 mMol) of (methoxymethyl)triphenylphosphonium chloride in 75 mL of dry tetrahydrofuran at −20° was added dropwise 14.0 mL (1.6M in toluene, 22 mMol) of potassium t-amylate solution. The reaction mixture was stirred for 1 hour then to the resulting red mixture was added dropwise over 10 minutes a solution of 3.96 g (18.5 mMol) of the title C compound in 10 mL of tetrahydrofuran. The reaction was stirred for 2 hours at −20° then warmed to 0° and quenched with 20 mL of water. The resulting mixture was concentrated to ~½ volume in vacuo then partitioned between 120 mL of water and 75 mL of ether. The organic layer was separated and the aqueous layer was extracted with an additional 75 mL of ether. The organic extracts were combined, washed with 50 mL of brine, dried over anhydrous magnesium sulfate and concentrated in vacuo. The residue was slurried with 100 mL of hexane and then filtered. The filtrate was concentrated in vacuo to give an oil. The crude material was purified by flash chromatography to afford 3.51 g (14.5 mMol) of the title D compound as a pale yellow liquid.

E. (cis)-3-Oxabicyclo[4.1.0]heptan-4-ol

To a solution of 1.50 g (6.2 mMol) of the title D compound in 5 mL of the tetrahydrofuran cooled in an ice-bath was added 5 mL of 1M aqueous hydrochloric acid solution. The reaction mixture was warmed to room temperature, stirred rapidly for 3.5 hours then quenched by addition of 600 mg (7.1 mMol) of solid sodium bicarbonate in small portions. The resulting mixture was partitioned between 10 mL of water and 15 mL of hexane. The aqueous layer was separated and the hexane layer was washed with two-10 mL portions of water. The aqueous layers were combined, saturated with solid sodium chloride and then extracted with five-20 mL portions of ether. The ether extracts were combined, dried over anhydrous magnesium sulfate and concentrated in vacuo (cold water bath) to afford 425 mg (3.73 mMol) of the title E compound as a pale yellow oil.

F. [1α(Z),2α]-7-[2-(Hydroxymethyl)cyclopropyl]-5-heptenoic acid, methyl ester To a mixture of 4.00 g (9.03 mMol) of (4-carboxybutyl)triphenylphosphonium bromide in 20 mL of dry tetrahydrofuran cooled in an ice-bath was added dropwise over 10 minutes 10.5 mL (1.6M in toluene, 17 mMol) of potassium t-amylate solution. The reaction mixture was stirred for 1 hour then to the resulting red-orange solution was added a solution of 410 mg (3.60 mMol) of the title E compound in 5 ml of tetrahydrofuran. After 1 hour the reaction was quenched by addition of 75 mL of 1M aqueous hydrochloric acid and the resulting mixture was extracted with two-50 mL portions of ether. The organic extracts were combined, dried over anhydrous magnesium sulfate and treated with excess ethereal diazomethane (until yellow color persisted) at 0°. The excess diazomethane was quenched with glacial acetic acid and the resulting solution concentrated in vacuo to give an oil. The crude oil was purified by flash chromatography to afford 530 mg (2.50 mMol) of the title F compound as a pale yellow oil.

G. [1α(Z),2α]-7-[2-[(1,3-Dioxo-2H-isoindol-2-yl)methyl]-cyclopropyl]-5-heptenoic acid, methyl ester A mixture of 515 mg (2.43 mMol) of the title F compound, 700 mg (2.67 mMol) of triphenylphosphine and 393 mg (2.67 mMol) of powdered phthalimide in 15 mL of dry methylene chloride was stirred at room temperature for 20 minutes (not completely homogeneous). The reaction mixture was cooled in an ice-bath and added dropwise was 525 μL (2.67 mMol) of diisopropylazodicarboxylate. The reaction was warmed to room temperature, stirred for 1 hour then concentrated in vacuo to give an oil. The crude oil was purified by flash chromatography to afford 635 mg (1.86 mMol) of the title G compound as a pale yellow oil.

H. [1α(Z),2α]-7-[2-(Aminomethyl)cyclopropyl]-5-heptenoic acid, methyl ester

To a solution of 630 mg (1.85 mMol) of the title G compound in 9 mL of 2:1 sieve-dried methanol/dry methylene chloride cooled in ice-bath was added 130 μL (4.1 mMol) of anhydrous hydrazine. The reaction mixture was warmed to room temperature, stirred for 4 hours then added was 10 mL of toluene and concentrated in vacuo to remove excess hydrazine. The dilution/concentration sequence was repeated with 10 mL of 1:1 toluene/methanol then two times with 10 mL portions of methanol. To the residue was added 10 mL of dry methanol and refluxed for 2 hours. The reaction mixture was cooled to room temperature and added dropwise was 0.30 mL (3.6 mMol) of concentrated hydrochloric acid, a precipitate formed. After 15 minutes the resulting slurry was filtered and the filtrate concentrated in vacuo. To the residue was added 5 mL of methanol and cooled in an ice-bath. The mixture was filtered to remove the solid which formed and the filtrate concentrated in vacuo to give an oil. The resulting oil was washed with two-15 mL portions of cold ether then concentrated in vacuo to give 370 mg (1.49 mMol) of the title H compound as a yellow oil.

I. N-(4-Phenyl-1-oxobutyl)glycine, ethyl ester

4-Phenylbutyric acid (2.46 g, 15 mmol) was dissolved in distilled tetrahydrofuran (70 ml) in an argon atmosphere. After cooling in an ice bath, carbonyl diimidazole (2.43 g, 15 mmol) was added and the mixture was stirred cold 1 hour and at room temperature 1 hour. The mixture was then cooled and glycine ethyl ester.hydrochloride (2.09 g, 15 mmol) and distilled triethylamine (2.1 ml, 15 mmol) were added. The mixture was left stirring overnight at room temperature. After removal of the solvent in vacuo, ethyl ether (200 ml) was added. The solution was washed with 1 N hydrochloric acid (70 ml), 0.5 N sodium hydroxide (70 ml) and saturated sodium chloride solution (70 ml), dried over anhydrous magnesium sulfate and freed of solvent in vacuo leaving the title I compound (3.13 g) as white crystalline material.

J. N-(4-Phenyl-1-oxobutyl)glycine

The title I compound (3.07 g, 12.3 mmol) was hydrolyzed with sodium hydroxide (5 g, 125 mmol) in water (60 ml). After stirring at room temperature 6 hours, neutral material was removed by washing with ethyl ether (2×50 ml). The aqueous solution was then acidified with concentrated hydrochloric acid solution. The product was extracted into chloroform (3×60 ml), dried over anhydrous magnesium sulfate and freed of solvent in vacuo leaving a white solid. This was recrystallized from ethyl acetate (10 ml) to give the title J compound (2.18 g), m.p. 99°–101° C.

K. N-(4-Cyclohexyl-1-oxobutyl)glycine

The title J compound was dissolved in glacial acetic acid (25 ml). Platinum oxide (0.1 g) was added and the solution was hydrogenated on a Parr shaker at up to 55 p.s.i. until hydrogen uptake ceased (6.5 hours). The catalyst was removed by filtration and the acetic acid was removed in vacuo. The product crystallized and was recrystallized from ethyl ether (20 ml) to give the title K compound (1.18 g), m.p. 85°–88° C.

L. [1α(Z),2α]-7-[2-[[[[(4-Cyclohexyl-1-oxobutyl)amino]acetyl]amino]methyl]cyclopropyl]-5-heptenoic acid, methyl ester To a solution of 340 mg (1.58 mMol) of the title K compound in 5 mL of dry methylene chloride cooled in an ice-bath was added in one portion 256 mg (1.58 mMol) of carbonyl diimidazole. The mixture was stirred for 1 hour during which time it became homogeneous. To the resulting solution was added a solution of 356 mg (1.44 mMol) of the title H compound in 5 mL of methylene chloride followed immediately by 225 μL (1.6 mMol) of sieve-dried triethylamine. The reaction mixture was stirred for 1 hour then added to 20 mL of 1 M aqueous hydrochloric acid and extracted with 30 mL of ethyl acetate. The organic extract was dried over anhydrous magnesium sulfate and concentrated in vacuo to give a yellow oil. The crude material was purified by flash chromatography to afford 360 mg (0.86 mMol) of the title compound as a white solid, m.p. 66°–68°.

EXAMPLE 2

[1α(Z),2α]-7-[2-[[[[(4-Cyclohexyl-1-oxobutyl)amino]acetyl]amino]methyl]cyclopropyl]-5-heptenoic acid To a solution of 350 mg (0.83 mMol) of the title compound from Example 1 in 6 mL of 2:1 tetrahydrofuran/water was added 70 mg (1.6 mMol) of lithium hydroxide monohydrate. The reaction mixture was stirred at room temperature for 14 hours then acidified with 3 mL of 1M aqueous hydrochloric acid. The resulting mixture was added to 15 mL of water and extracted with two-15 mL portions of ethyl acetate. The organic extracts were combined, dried over anhydrous magnesium sulfate and concentrated in vacuo to afford 320 mg (0.79 mMol) of the title compound as a pale yellow oil.

Analysis calc'd for $C_{23}H_{38}N_2O_4$:
C, 67.94; H, 9.42; N, 6.89;
Found: C, 67.49; H, 8.97; N, 6.96.

EXAMPLE 3

[1α(Z),2α-6-[2-[[[[(4-Cyclohexyl-1-oxobutyl)amino]acetyl]amino]methylcyclopropyl]-4-hexenoic acid, methyl ester

A. (Carboxypropyl)triphenylphosphonium bromide

A mixture of 100 g of 4-bromobutyric acid and 156.9 g of triphenylphosphine was heated under argon at 130° C. for 2 hours. The cooled reaction mixture was suspended in 250 mL of chloroform and heated to reflux, then diluted with 200 mL of ether. This was stirred for 30 minutes at room temperature, chilled to 0° C, and filtered. The solid was dried in vacuo to afford 240 g title salt.

B. [1α(Z),2α]-6-[(2-(Hydroxymethyl)cyclopropyl]-4-hexenoic acid, methyl ester To a mixture of 5.00 g (11.7 mMol) of the title A compound in 40 mL of dry tetrahydrofuran cooled in an ice-bath was added dropwise 13 mL (1.6M in toluene, 21 mMol) of potassium t-amylate solution over 10 minutes. The reaction mixture was stirred for 45 minutes then to the resulting yellow slurry was added dropwise a solution of 470 mg (4.12 mMol) of the title E compound from Example 1 in 5 mL of tetrahydrofuran. The reaction mixture was stirred for 1 hour then quenched by the addition of 20 mL of 1M aqueous hydrochloric acid. The resulting mixture was added to 100 mL of 1M aqueous hydrochloric acid and extracted with three-40 mL portions of ether. The combined ether extracts were dried over anhydrous magnesium sulfate then cooled in an ice-bath and treated with excess ethereal diazomethane. The excess diazomethane was quenched with glacial acetic acid and the resulting solution was concentrated in vacuo to give a yellow oil. The crude material was purified by flash chromatography to afford 655 mg (3.31 mMol) of the title B compound as a pale yellow oil.

[1α(Z),2]-6-2-[[[[(4-Cyclohexyl-1-oxobutyl)amino]acetyl]amino]methylcyclopropyl]4-hexenoic acid, methyl ester The title compound for this Example 3 was obtained by using the title B compound provided above and the procedures outlined in parts G through L of Example 1.

EXAMPLE 4

[1α(Z),2α]-6-2-[[[[(4-Cyclohexyl-1-oxobutyl)amino]acetyl]amino]methyl]cyclopropyl]-4-hexenoic acid The title compound for this Example 4 was obtained by using the title compound of Example 3 and the procedure outlined in Example 2.

EXAMPLES 5-25

The following additional compounds within the scope of the present invention can be made using the procedures outlined in Examples 1-4 and above.

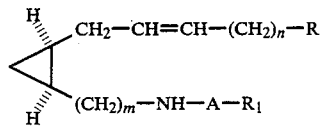

| Ex. No. | R | $R_1$ | A | m | n |
|---|---|---|---|---|---|
| 5 | (OH)-S(=O)2-CH3) | $CH_2-N(H)-C(=O)-C_7H_{15}$ | $-C(=O)-$ | 1 | 2 |
| 6 | $CO_2H$ | $-(CH_2)_2-N(H)-C(=O)-C_5H_{11}$ | single bond | 1 | 3 |
| 7 | $CO_2Na$ | | $-S(=O)_2-$ | 1 | 2 |
| 8 | ![](tetrazole with CH3) | " | " | 1 | 3 |

-continued
| Ex. No. | R | R₁ | A | m | n |
|---|---|---|---|---|---|
| 9 | $CO_2H$ | 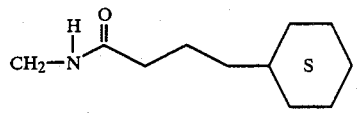 |  | 1 | 2 |
| 10 | $CO_2H$ | 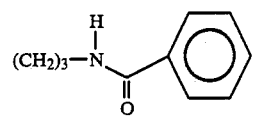 | single bond | 1 | 2 |
| 11 | $CO_2Li$ | 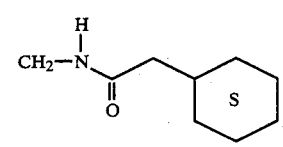 |  | 1 | 3 |
| 12 | 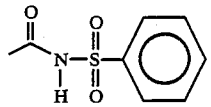 | 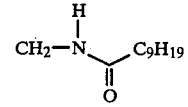 |  | 1 | 2 |
| 13 | $CO_2H$ | $-CH_3$ |  | 1 | 3 |
| 14 | 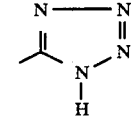 | 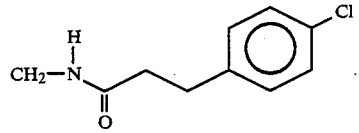 |  | 1 | 2 |
| 15 | $CO_2H$ | 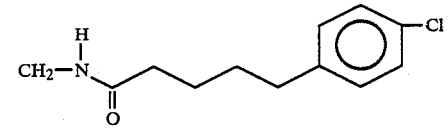 |  | 1 | 2 |
| 16 | " | 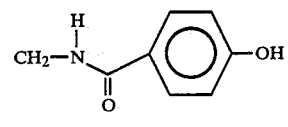 | single bond | 1 | 2 |
| 17 | " | 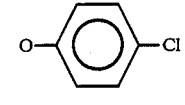 |  | 1 | 3 |
| 18 | " | $-OC_7H_{15}$ |  | 1 | 2 |
| 19 | " | 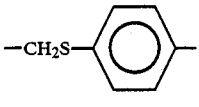 | " | 1 | 2 |
| 20 | " | 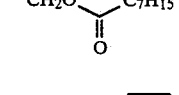 | " | 1 | 2 |
| 21 | 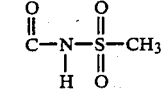 | 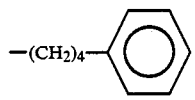 | single bond | 1 | 3 |

-continued

| Ex. No. | R | R₁ | A | m | n |
|---|---|---|---|---|---|
| 22 | CO₂H | -C₆H₄-CH₃ (para) | $-S(=O)_2-$ | 1 | 2 |
| 23 | 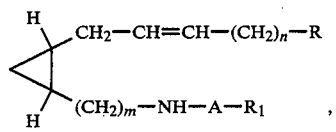 | —O—C₇H₁₅ | $-C(=O)-$ | 1 | 2 |
| 24 | CO₂H | -S-C₆H₅ | " | 1 | 3 |
| 25 | CO₂Na | 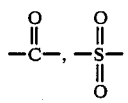CH₂—NH—C(=O)—C₆H₅ | " | 1 | 3 |

What is claimed is:

1. A compound of the formula

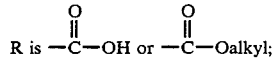

including pharmaceutically acceptable salts thereof, wherein

R is —C(=O)—OH, —C(=O)—Oalkali metal, —C(=O)—Oalkyl, $$-\overset{O}{\underset{}{C}}-\overset{H}{\underset{}{N}}-\overset{O}{\underset{O}{S}}-R_2 \text{ or 5-tetrazolyl;}$$

R₁ is alkyl, —(CH₂)q—R₂, —(CH₂)q—S(O)r—R₂,

—(CH₂)q—O—R₃, —(CH₂)q—O—C(=O)—C₇H₁₅ or

—(CH₂)q—N(H)—C(=O)—R₂;

R₂ is aryl, alkyl or cycloalkyl;
R₃ is aryl, alkyl or cycloalkyl;
A is $$-\overset{O}{\underset{}{C}}-, \quad -\overset{O}{\underset{O}{S}}-$$

or a single bond;
m is an integer from 1 to 2;
n is an integer from 2 to 4;

q is an integer from 1 to 4, except when A=single bond then q is an integer from 2-4; and r is zero or an integer from 1 to 2;

wherein the (CH₂)ₘ and (CH₂)ₙ groups may be substituted with one or two alkyl and/or one or two alkoxy substituents;

the term cycloalkyl refers to saturated cyclic hydrocarbon groups having 3 to 12 carbon atoms which may include 1 or 2 substituents independently selected from halogen, alkyl and alkoxy; and, the term aryl refers to monocyclic or bicyclic aromatic groups containing from 6 to 10 carbon atoms in the ring portion which may include 1 or 2 substituents independently selected from alkyl, halogen and alkoxy.

2. A compound of claim 1 wherein

R is —C(=O)—OH or —C(=O)—Oalkyl;

R₁ is (CH₂)q—NH—C(=O)—R₂;

A is —C(=O)—.

3. A compound of claim 1 wherein

R is —C(=O)—OH;

R₁ is —CH₂—NH—C(=O)—(CH₂)₃—cyclohexyl;

A is —C(=O)—;

m=1; and,
n=2 or 3.

4. A compound of claim 1 having the name [1α(Z)-,2α]-7-[2-[[[[(4-cyclohexyl-1-oxobutyl)amino]acetyl]amino]methyl]cyclopropyl]-5-heptenoic acid, methyl ester.

5. A compound of claim 1 having the name [1α(Z)-,2α]-7-[2-[[[[(4-cyclohexyl-1-oxobutyl)amino]acetyl]amino]methyl]cyclopropyl]-5-heptenoic acid.

6. A compound of claim 1 having the name [1α(Z)-,2α]-6-[2-[[[(4-cyclohexyl-1-oxobutyl)amino]acetyl]amino]methylcyclopropyl]-4-hexenoic acid, methyl ester.

7. A compound of claim 1 having the name [1α(Z)-,2α]-6-[2-[[[(4-cyclohexyl-1-oxobutyl)amino]acetyl]amino]methyl]cyclopropyl]-4-hexenoic acid.

8. A method of inhibiting arachidonic acid-induced platelet aggregation and bronchoconstriction, which comprises administering to the circulatory system of a mammalian host an effective amount of a compound as defined in claim 1 of a pharmaceutically acceptable salt thereof.

9. The method as defined in claim 8 wherein said compound is administered in an amount within the range of from about 0.1 to about 100 mg/kg.

10. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier thereof.

11. A method of inhibiting platelet aggregation which comprises administering to a mammalian host an effective amount of a compound as defined in claim 1 or a pharmaceutically acceptable salt thereof.

12. A method of inhibiting bronchoconstriction associated with asthma, which comprises administering to a mammalian host an effective amount of a compound as defined in claim 1 or a pharmaceutically acceptable salt thereof.

13. A method of treating peripheral vascular diseases, which comprises topically or systemically administering to a mammalian host an effective amount of a compound as defined in claim 1 or a pharmaceutically acceptable salt thereof.

* * * * *